United States Patent
Pearl, Jr. et al.

(10) Patent No.: US 11,047,225 B2
(45) Date of Patent: Jun. 29, 2021

(54) IN SITU MONITORING OF CEMENT SLURRY LOCATIONS AND SETTING PROCESSES

(71) Applicant: Halliburton Energy Services, Inc., Houston, TX (US)

(72) Inventors: William C. Pearl, Jr., Spring, TX (US); Megan Renee Pearl, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 34 days.

(21) Appl. No.: 16/535,292

(22) Filed: Aug. 8, 2019

(65) Prior Publication Data

US 2019/0360321 A1    Nov. 28, 2019

Related U.S. Application Data

(62) Division of application No. 15/313,266, filed as application No. PCT/US2014/052627 on Aug. 26, 2014, now Pat. No. 10,415,370.

(51) Int. Cl.
*E21B 47/005* (2012.01)
*C09K 8/42* (2006.01)
(Continued)

(52) U.S. Cl.
CPC ............ *E21B 47/005* (2020.05); *C04B 28/02* (2013.01); *C04B 40/0032* (2013.01);
(Continued)

(58) Field of Classification Search
CPC ...... E21B 47/005; E21B 47/006; E21B 47/00; C04B 40/0096; G01N 33/383
See application file for complete search history.

(56) References Cited

U.S. PATENT DOCUMENTS

| 4,618,939 A | 10/1986 | Davis |
| 5,027,267 A | 6/1991 | Pitts et al. |

(Continued)

FOREIGN PATENT DOCUMENTS

| CN | 1904310 A | 1/2007 |
| CN | 102334024 A | 1/2012 |

(Continued)

OTHER PUBLICATIONS

China Application Serial No. 2013800790136; Fourth Office Action; dated Mar. 21, 2019, 6 pages.
(Continued)

*Primary Examiner* — Catherine Loikith
(74) *Attorney, Agent, or Firm* — Gilliam IP PLLC

(57) ABSTRACT

Optical analysis devices may be configured for optically interacting a set cement with a chemical filter and a detector that together are configured to detect a characteristic of the set cement, wherein optically interacting the set cement with the chemical filter comprises absorbing, by the chemical filter, at least a portion of an electromagnetic radiation having optically interacted with the set cement. Relative to cementing operations, such optical analysis devices may be useful in identifying fluids, analyzing compositions of cement slurries, investigating the status of a reaction occurring in a cement slurry, detecting and/or monitoring corrosion of a set cement, and the like.

17 Claims, 4 Drawing Sheets

(51) Int. Cl.
*G01N 33/38* (2006.01)
*G01N 21/75* (2006.01)
*C04B 40/00* (2006.01)
*E21B 33/13* (2006.01)
*E21B 47/113* (2012.01)
*C04B 28/02* (2006.01)
*E21B 33/14* (2006.01)

(52) U.S. Cl.
CPC .......... *C04B 40/0096* (2013.01); *C09K 8/42* (2013.01); *C09K 8/424* (2013.01); *E21B 33/13* (2013.01); *E21B 33/14* (2013.01); *E21B 47/113* (2020.05); *G01N 21/75* (2013.01); *G01N 33/383* (2013.01)

(56) References Cited

U.S. PATENT DOCUMENTS

| | | |
|---|---|---|
| 5,167,149 A | 12/1992 | Mullins et al. |
| 5,400,137 A | 3/1995 | Winslow et al. |
| 5,418,614 A | 5/1995 | Brost et al. |
| 5,489,977 A | 2/1996 | Winslow et al. |
| 5,859,430 A | 1/1999 | Mullins et al. |
| 6,176,323 B1 | 1/2001 | Weirich et al. |
| 6,198,531 B1 | 3/2001 | Myrick et al. |
| 6,529,276 B1 | 3/2003 | Myrick |
| 6,614,360 B1 | 9/2003 | Leggett et al. |
| 7,123,844 B2 | 10/2006 | Myrick |
| 7,138,156 B1 | 11/2006 | Myrick et al. |
| 7,219,729 B2 | 5/2007 | Bostick, III et al. |
| 7,472,748 B2 | 1/2009 | Gdanski et al. |
| 7,623,233 B2 | 11/2009 | Freese et al. |
| 7,697,141 B2 | 4/2010 | Jones et al. |
| 7,712,527 B2 | 5/2010 | Roddy |
| 7,834,999 B2 | 11/2010 | Myrick et al. |
| 7,911,605 B2 | 3/2011 | Myrick et al. |
| 7,920,258 B2 | 4/2011 | Myrick et al. |
| 7,938,175 B2 | 5/2011 | Skinner et al. |
| 8,049,881 B2 | 11/2011 | Myrick et al. |
| 8,132,452 B1 | 3/2012 | Selman et al. |
| 8,141,633 B2 | 3/2012 | Hampton et al. |
| 8,212,213 B2 | 7/2012 | Myrick et al. |
| 8,212,216 B2 | 7/2012 | Perkins et al. |
| 8,213,006 B2 | 7/2012 | Myrick et al. |
| 8,237,920 B2 | 8/2012 | Jones et al. |
| 2006/0027144 A1 | 2/2006 | Chatterji et al. |
| 2006/0142955 A1 | 6/2006 | Jones et al. |
| 2007/0282647 A1 | 12/2007 | Freese et al. |
| 2008/0231849 A1 | 9/2008 | Myrick et al. |
| 2008/0276687 A1 | 11/2008 | Myrick et al. |
| 2009/0073433 A1 | 3/2009 | Myrick et al. |
| 2009/0097024 A1 | 4/2009 | Blackburn et al. |
| 2009/0140144 A1 | 6/2009 | Myrick et al. |
| 2009/0182693 A1 | 7/2009 | Fulton et al. |
| 2009/0216504 A1 | 8/2009 | Priore et al. |
| 2009/0219512 A1 | 9/2009 | Myrick et al. |
| 2009/0219538 A1 | 9/2009 | Myrick et al. |
| 2009/0219539 A1 | 9/2009 | Myrick et al. |
| 2009/0250613 A1 | 10/2009 | Myrick et al. |
| 2009/0299946 A1 | 12/2009 | Myrick et al. |
| 2009/0316150 A1 | 12/2009 | Myrick et al. |
| 2010/0012316 A1 | 1/2010 | Schlachter |
| 2010/0050905 A1 | 3/2010 | Lewis et al. |
| 2010/0051266 A1 | 3/2010 | Roddy et al. |
| 2010/0051275 A1 | 3/2010 | Lewis et al. |
| 2010/0073666 A1 | 3/2010 | Perkins et al. |
| 2010/0141952 A1 | 6/2010 | Myrick et al. |
| 2010/0148785 A1 | 6/2010 | Schaefer et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0186955 A1 | 7/2010 | Saasen et al. |
| 2010/0195105 A1 | 8/2010 | Myrick et al. |
| 2010/0245096 A1 | 9/2010 | Jones et al. |
| 2010/0265509 A1 | 10/2010 | Jones et al. |
| 2010/0302539 A1 | 12/2010 | Myrick et al. |
| 2010/0305741 A1 | 12/2010 | Myrick |
| 2010/0328669 A1 | 12/2010 | Myrick et al. |
| 2011/0108720 A1 | 5/2011 | Ford et al. |
| 2011/0132606 A1 | 6/2011 | Demong et al. |
| 2011/0139464 A1 | 6/2011 | Henderson et al. |
| 2011/0192594 A1 | 8/2011 | Roddy et al. |
| 2011/0199610 A1 | 8/2011 | Myrick et al. |
| 2011/0308788 A1 | 12/2011 | Ravi et al. |
| 2012/0037428 A1 | 2/2012 | Plop |
| 2012/0150451 A1 | 6/2012 | Skinner et al. |
| 2012/0158310 A1 | 6/2012 | Adams et al. |
| 2012/0181420 A1 | 7/2012 | Duncan et al. |
| 2012/0191354 A1 | 7/2012 | Caycedo |
| 2012/0205103 A1 | 8/2012 | Ravi et al. |
| 2012/0222852 A1 | 9/2012 | Pelletier |
| 2013/0031964 A1 | 2/2013 | Tunheim et al. |
| 2013/0032345 A1 | 2/2013 | Freese et al. |
| 2013/0032545 A1 | 2/2013 | Freese et al. |
| 2013/0213638 A1 | 8/2013 | Keller et al. |
| 2013/0284901 A1 | 10/2013 | Freese et al. |
| 2013/0284904 A1 | 10/2013 | Freese et al. |
| 2014/0008013 A1 | 1/2014 | Dai et al. |
| 2014/0076549 A1 | 3/2014 | Pelletier et al. |

FOREIGN PATENT DOCUMENTS

| | | |
|---|---|---|
| CN | 102334624 A | 2/2012 |
| EP | 1057118 B1 | 8/1999 |
| EP | 2491227 A1 | 4/2011 |
| JP | 2007535655 A | 12/2007 |
| JP | 2009524814 A | 1/2010 |
| WO | 2011049571 A1 | 4/2011 |
| WO | 2013155061 A1 | 10/2013 |
| WO | 2014052182 A1 | 4/2014 |
| WO | 2015047247 A1 | 4/2015 |
| WO | 2016032437 A1 | 3/2016 |
| WO | 2016032438 A1 | 3/2016 |

OTHER PUBLICATIONS

India Application Serial No. 201617004711, Office Action, dated May 28, 2019, 6 pages.
Mexican Application Serial No. MX/a/2016/001841; First Office Action; dated Apr. 10, 2019, 4 pages.
PCT Application Serial No. PCT/US2013/061668, International Search Report, dated Jul. 4, 2014, 3 pages.
PCT Application Serial No. PCT/US2013/061668, Written Opinion, dated Jul. 4, 2014, 10 pages.
PCT Application Serial No. PCT/US2014/052627, International Search Report, dated May 27, 2015, 3 pages.
PCT Application Serial No. PCT/US2014/052627, Written Opinion, dated May 27, 2015, 11 pages.
PCT Application Serial No. PCT/US2014/052640, International Search Report, dated May 27, 2015, 3 pages.
PCT Application Serial No. PCT/US2014/052640, Written Opinion, dated May 27, 2015, 10 pages.
U.S. Appl. No. 14/890,670, Final Rejection, dated Apr. 3, 2019, 30 pages.
U.S. Appl. No. 14/890,670, Final Rejection, dated Apr. 5, 2018, 38 pages.
U.S. Appl. No. 14/890,670, Final Rejection, dated Aug. 8, 2019, 28 pages.
U.S. Appl. No. 14/890,670, Non-Final Office Action, dated Sep. 19, 2018, 29 pages.
U.S. Appl. No. 14/890,670, Non-Final rejection, dated Oct. 18, 2017, 34 pages.
U.S. Appl. No. 15/313,266, Non-Final Rejection, dated Nov. 28, 2018, 10 pages.
U.S. Appl. No. 15/313,283, Non-Final Rejection, dated Nov. 16, 2018, 8 pages.
China Application Serial No. 2013800790136; China Search; Jan. 10, 2018, 1 page.
Japan Application No. 2016534567, Notification of Reasons for Refusal, dated Jan. 2017, 2 Pages.

(56) References Cited

OTHER PUBLICATIONS

Australia Patent Application No. 2013402071, Patent Examination Report No. 1, dated May 9, 2016, 3 Pages.
CA Application No. 2,920,602, Examiner Requisition, dated Jan. 24, 2017, 4 pages.
China Application Serial No. 2013800790136; Second Office Action; dated Aug. 17, 2018, 5 pages.
China Application Serial No. 2013800790136; Third Office Action; dated Dec. 25, 2018, 9 pages.
China Application Serial No. 2013800790136; First Office Action; dated Jan. 19, 2018, 8 pages.
Brooke, et al., "Multimode Imaging in the Thermal Infrared for Chemical Contrast Enhancement. Part 1: Methodology", Anal. Chem., 2010, 82 (20), pp. 8412-8420, DOI: 10.1021/ac101109w, Sep. 23, 2010.
Brooke, et al., "Multimode Imaging in the Thermal Infrared for Chemical Contrast Enhancement. Part 2: Simulation Driven Design", Anal. Chem., 2010, 82 (20), pp. 8421-8426, DOI: 10.1021/ac101108z., Sep. 23, 2010.
Brooke, et al., "Multimode Imaging in the Thermal Infrared for Chemical Contrast Enhancement. Part 3: Visualizing Blood on Fabrics", Anal. Chem., 2010, 82 (20), pp. 8427-8431, DOI: 10.1021/ac101107v., Sep. 23, 2010.
Brost, et al., "Optical Methods for Monitoring Treating Chemicals in Oilfield Water Systems", Society of Petroleum Engineers, 1991, 16 pages.
Dai, et al., "Molecular Factor Computing for Predictive Spectroscopy", Pharmaceutical Research, 2007.
Dai, "Simulations-Guided Design of Process Analytical Sensor Using Molecular Factory Computing", University of Kentucky Doctoral Dissertations, Paper 483, 2007.
Myrick, et al., "Spectral Tolerance Determination for Multivariate Optical Element Design", Fresenuis' Journal of Analytical Chemistry, 369:2001, 5 pages.
Ramchandran, et al., "Chemical Kinetics in Real Time: Using the Differential Rate Law and Discovering the Reaction Orders", A Physical Chemistry Laboratory Experiment, Journal of Chemical Education, 1996, pp. 686-689.
Simcock, et al., "Tuning D* with Modified Thermal Detectors", https://doi.org/10.1366/000370206779321481, Dec. 1, 2006.
Soyemi, et al., "Design and Testing of a Multivariate Optical Element: The First Demonstration of Multivariate Optical Computing for Predictive Spectroscopy", Analytical Chemistry, American Chemical Society, US, vol. 73, No. 6,, Feb. 10, 2001, 1069-1079.
GB Application Serial No. GB1602456.4, Examination Report Under Section 18(3), dated Nov. 12, 2019, 3 pages.

IN SITU MONITORING OF CEMENT SLURRY LOCATIONS AND SETTING PROCESSES

BACKGROUND

The exemplary embodiments described herein relate to optical analysis systems and methods for analyzing fluids.

Cementing operations are often used in wellbores for, inter alia, supporting casings and liners, providing zonal isolation, and protecting the casing from corrosive formation fluids. In such operations, it is often important to precisely know the location, characteristics, and setting status of cement slurries as they circulate and set in wellbores or other annuli therein. In situ analysis of cement slurries during cementing operations is often not achievable with conventional monitoring systems, which are incapable of operation in extreme environments such as downhole applications. Accordingly, the location, characteristics, and setting status of cement slurries are often required to be extrapolated from laboratory data, calculations of volumes to be filled, and calculations based on the conditions in the wellbore (e.g., temperature).

After the cementing operation has completed, the location, characteristics, and setting status of a cement slurry (or set cement) can be analyzed via logging techniques, which are time-consuming and costly. For example, if the cementing operation was successfully performed (e.g., the proper locations were cemented) and the cement is sufficiently set, subsequent subterranean operations can be performed (e.g., drilling operations, fracturing operations, completion operations, and the like). However, if an aspect of the cementing operation was incorrect, remedial operations are often necessary.

For example, if the cement is not sufficiently set, the operator allows for additional setting time and then runs another logging operation, which further contributes to costs and nonproductive time.

In another example, if too much cement slurry was added, a drill-out operation may be required, which is particularly prevalent in reverse cementing where the cement is pumped from the annulus side. In other instances, if too little cement slurry was added, another cementing operation may be needed.

These issues can be especially complex in normal primary cementing operations where the cement slurry is pumped down the casing and up the annulus. Generally, the cement slurry formulations are designed so that the 'lead' slurry (i.e., uppermost slurry after placement in the annulus) is of lower density than the 'tail' slurry that is the bottommost slurry placed near the bottom of the annulus. Proper placement of the 'lead' slurry behind casing and the sufficient setting of the cement near the casing shoe (i.e., near the bottom of the casing) are important for the casing to withstand pressures of the initial pressure test and subsequent drilling that are performed.

In other cementing operations, e.g., some remedial operations to plug thief zones, two fluids are utilized that, when contacted, viscosify and plug high permeability regions in the wellbore. Pumping calculated volumes is often insufficient to assure operation efficacy, which can lead to additional remedial operations and the use of high volumes of expensive fluids. Accordingly, in situ monitoring of the location of each of these fluids may reduce the cost and time associated with such remedial cementing operations.

As a whole, cementing operations are often performed multiple times during the lifetime of a well. Therefore, in situ analysis of cement slurries and/or set cements may have a compounding effect on reducing the cost and time associated with the drilling and maintenance of a well.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
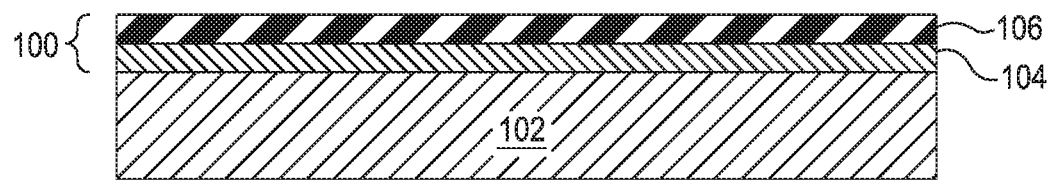
FIG. 1 illustrates an exemplary molecular factor computing element, according to one or more embodiments.

The exemplary embodiments described herein relate to optical analysis systems and methods that utilize molecular factor computing ("MFC") techniques in detecting and measuring in or near real-time the characteristics, including compositions, of the fluids used in cementing operations.

The exemplary systems and methods described herein employ various configurations of optical analysis devices, also commonly referred to as "opticoanalytical devices," for the real-time or near real-time monitoring of fluids in order to ascertain the location of a cement slurry and/or the status of a cement setting process. In operation, the exemplary systems and methods may be useful and otherwise advantageous in determining that a cement slurry has been properly placed, for example, in a wellbore, by monitoring a characteristic of the cement slurry and/or a spacer fluid introduced into the wellbore before or after the cement slurry. In other embodiments, the systems and methods may provide a real-time or near real-time determination of cement setting process kinetics, including the concentration of unreacted reagents and/or resultant products.

The optical analysis devices, which are described in more detail below, can advantageously provide real-time or near real-time monitoring of a cement slurry or other fluid relating thereto (e.g., a spacer fluid) and chemical reactions occurring therein that cannot presently be achieved with either onsite analyses at a job site or via more detailed analyses that take place in a laboratory. A significant and distinct advantage of these devices is that they can be configured to specifically detect and/or measure a particular characteristic of interest of a fluid or other material, thereby allowing qualitative and/or quantitative analyses of the fluid to occur without having to extract a sample and undertake time-consuming analyses at an off-site laboratory. With the ability to undertake real-time or near real-time analyses, the exemplary systems and methods described herein may be able to provide some measure of proactive or responsive control over the cement slurry location, provide some measure of cement slurry loss into the subterranean formation as an indicator of wellbore damage, eliminate time-consuming wireline operations that analyze the progress of the setting processes of cement slurries, mitigate drill-out operations as a result of excess cement slurry introduction into the wellbore, enable the collection and archival of information relating to cement setting processes in conjunction with operational information to optimize subsequent operations, and/or enhance the capacity for remote job execution.

Those skilled in the art will readily appreciate that the systems and methods disclosed herein may be suitable for use in the oil and gas industry since the described optical analysis devices provide a relatively low cost, rugged, and accurate means for monitoring fluids and chemical reactions occurring therein in order to facilitate the efficient management of wellbore operations involving cement slurries. It will be further appreciated, however, that the various disclosed systems and methods are equally applicable to other technology or industry fields including, but not limited to, the construction industry, industrial applications, mining industries, or any field where it may be advantageous to determine in real-time or near real-time the status of the cement setting processes or other similar chemical reactions.

The optical analysis devices suitable for use in the present embodiments can be deployed at any number of various points within a flow path to monitor a fluid including, but not limited to, the location of a cement slurry, the location of a spacer fluid introduced before or after a cement slurry, and/or the status of the cement setting process. It should be noted that the location of a material of interest can be derived from detecting a characteristic of interest with an optical analysis device having a known location (approximate or exact) or using two or more optical analysis devices having known relative locations to each other. Depending on the location of the particular optical analysis device, various types of information about the cement slurry can be ascertained. In some cases, for example, the optical analysis devices can be used to monitor a chemical reaction in real-time that relates to cement setting processes, for example, by determining the concentration of unreacted reagents and any resulting products relating to the cement setting process. This may prove advantageous in determining when the cement setting process has progressed to completion. It is known to those skilled in the art that while true completion of cement hydration may take a long time often extending into months, for the purpose of cementing operations (e.g., subterranean cementing operations), the completion of cement hydration is taken as that phase in cement hydration at which point the strength development values (e.g., compressive strength) reach a plateau value, which may, in some instance, take about 2 to about 28 days. In some embodiments, the cement hydration level and indication of strength may be characterized by the concentration of cement hydration products (e.g., calcium hydroxide or calcium silicate hydrates in the case of Portland cements). Thus, the systems and methods described herein may be configured to monitor a fluid and a chemical reaction processes related thereto.

Additionally, monitoring the location of the cement slurry or other suitable fluid downhole may be used to determine lost circulation zones extending from the wellbore. For example, lost circulation zones may be identified comparing a predicted location of the fluid based on flow rate and flow path dimensions and the actual location of the fluid based on analysis with the optical analysis devices where a delay in the fluid reaching a predicted location may indicate a lost circulation zone has been encountered.

Further, the optical analysis devices may also be configured to measure the long-term characteristics of the set cement. For example, the optical analysis device may be configured to measure and monitor the level of carbonation in $CO_2$ wells. The carbonation corrodes the set cement. Therefore, if needed, remedial operations may be performed to proactively offset the corrosive effects of carbonation before serious situations like cracking or even failure occur.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid (e.g., a spacer fluid, a cement fluid composition, a lost circulation treatment fluid, and the like) or a formation fluid as found in the oil and gas industry. Fluids can include various flowable mixtures of solids, liquids, and/or gases. Illustrative gases that can be considered fluids according to the present embodiments include, for example, air, nitrogen, carbon dioxide, argon, helium, hydrogen sulfide ($H_2S$), methane, ethane, butane, and other hydrocarbon gases, combinations thereof and/or the like.

As used herein, the term "cement fluid composition" refers to any fluid that comprises a cement. Cement is not necessarily hydraulic cement, since other types of materials (e.g., polymers like epoxies and latexes) can be used in place of, or in addition to, a hydraulic cement. Examples of cements may include, but are not limited to, hydraulic cements, Portland cements, gypsum cements, calcium phosphate cements, high alumina content cements, silica cements, high alkalinity cements, shale cements, acid/base cements, magnesia cements (e.g., Sorel cements), fly ash cements, zeolite cement systems, cement kiln dust cement systems, slag cements, micro-fine cements, epoxies, bentonites, latexes, and the like, any derivative thereof, and any combination thereof. Cement fluid compositions may be cement slurries that include water or dry cement blends. Unless otherwise specified, the term "fluid" encompasses cement fluid compositions, the term "cement fluid compositions" encompasses cement slurries and dry cement blends, and the term "cement slurry" encompasses foamed cements. As used herein, the term "dry cement blend" refers to a mixture of solid particles including at least some cement particles and is not hydrated beyond about ambient conditions (e.g., no additional water has been added).

As used herein, the term "chemical reaction process" or "chemical reaction" refers to a process that leads to the transformation of one set of chemical substances to another. As known to those skilled in the art, chemical reactions involve one or more reagents, as described below, that chemically react either spontaneously, requiring no input of energy, or non-spontaneously typically following the input of some type of energy, such as heat, light, or electricity. The chemical reaction process yields one or more products, which may or may not have properties different from the reagents.

As used herein, the term "cement setting process" refers to the chemical reaction(s) that cause a cement slurry to harden into a cement. Chemical reactions of cement setting processes described herein may include, but are not limited to, hydration reactions (e.g., reactions between hydraulic cements and water), crosslinking reactions (e.g., polymer crosslinking reactions and reactions between 2-component epoxies), and the like, and any combination thereof. As used herein, the term "hydraulic cement" refers to a cement that hardens in the presence of water. Changes in characteristics that may be useful in providing the status of a cement setting process may include, but are not limited to, an increase in particle size, a plateau of an exothermic reaction, a decrease in the concentration of a reagent (e.g., water), an increase in the concentration of a product (e.g., a base like calcium hydroxide), and the like, and any combination thereof.

As used herein, the term "cementing operation" encompasses any subterranean operation utilizing a cement slurry for example in primary cementing operations, secondary cementing operations, squeeze operations, remedial cementing operations, casing operations, plugging operations (e.g., relative to thief zones), lost circulation operations, zonal isolation operations, and the like, including any of the foregoing with traditional or reverse fluid flow directions.

As used herein, the term "characteristic" refers to a chemical, mechanical, or physical property (quantitative or qualitative) of a material of interest (e.g., a spacer fluid, a cement fluid composition, a lost circulation treatment fluid, and the like) or analyte thereof. As used herein, the term "analyte" refers to a chemical component of the material of interest. The term analyte encompasses both chemical components involved in a chemical reaction (e.g., reagents and products) and chemical components not involved in a chemical reaction transpiring within the material of interest. Illustrative characteristics of a material of interest that can be monitored with the optical analysis devices disclosed herein can include, for example, chemical composition (e.g., identity and concentration in total or of individual analytes), impurity content, pH, viscosity, density, ionic strength, total dissolved solids, salt content, porosity, opacity, bacteria content, particle size distribution, color, temperature, hydration level, oxidation state, and the like. Moreover, the phrase "characteristic of interest" may be used herein to refer to a characteristic of the cement slurry or analyte thereof, a characteristic of a spacer fluid or analyte thereof, a characteristic of a treatment or drilling fluid or analyte thereof, and/or a characteristic of a chemical reaction transpiring or otherwise occurring therein.

Exemplary analytes may include, but are not limited to, water, salts, minerals (wollastonite, metakaolin, and pumice), cements (Portland cements, gypsum cements, calcium phosphate cements, high alumina content cements, silica cements, and high alkalinity cements), fillers (e.g., fly ash, fume silica, hydrated lime, pozzolanic materials, sand, barite, calcium carbonate, ground marble, iron oxide, manganese oxide, glass bead, crushed glass, crushed drill cutting, ground vehicle tire, crushed rock, ground asphalt, crushed concrete, crushed cement, ilmenite, hematite, silica flour, fume silica, fly ash, elastomers, polymers, diatomaceous earth, a highly swellable clay mineral, nitrogen, air, fibers, natural rubber, acrylate butadiene rubber, polyacrylate rubber, isoprene rubber, chloroprene rubber, butyl rubber, brominated butyl rubber, chlorinated butyl rubber, chlorinated polyethylene, neoprene rubber, styrene butadiene copolymer rubber, sulphonated polyethylene, ethylene acrylate rubber, epichlorohydrin ethylene oxide copolymer, ethylene propylene rubber, ethylene propylene diene terpolymer rubber, ethylene vinyl acetate copolymer, flourosilicone rubber, silicone rubber, poly-2,2,1-bicycloheptene (polynorbomeane), alkylstyrene, crosslinked substituted vinyl acrylate copolymer, nitrile rubber (butadiene acrylonitrile copolymer), hydrogenated nitrile rubber, fluoro rubber, perfluoro rubber, tetraflouroethylene/propylene, starch polyacrylate acid graft copolymer, polyvinyl alcohol cyclic acid anhydride graft copolymer, isobutylene maleic anhydride, acrylic acid type polymer, vinylacetate-acrylate copolymer, polyethylene oxide polymer, carboxymethyl cellulose polymer, starch-polyacrylonitrile graft copolymer, polymethacrylate, polyacrylamide, and non-soluble acrylic polymer), hydrocarbons, acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, cement slurry loss control additives, gas migration control additives, gases, air, nitrogen, carbon dioxide, hydrogen sulfide ($H_2S$), argon, helium, hydrocarbon gases, methane, ethane, butane, catalysts, clay control agents, chelating agents, corrosion inhibitors, dispersants, flocculants, scavengers (e.g., $H_2S$ scavengers, $CO_2$ scavengers, or $O_2$ scavengers), lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, paraffin waxes, asphaltenes, foams, sand or other solid particles, and the like. Combinations of these components can be used as well.

As used herein, the term "flow path" refers to a route through which a fluid is capable of being transported between two points. In some cases, the flow path need not be continuous or otherwise contiguous between the two points. Exemplary flow paths include, but are not limited to, a slurry tank, a flowline, a pipeline, a conduit, a wellbore annulus (e.g., an annulus between a casing and a wellbore or an annulus between a screen and a wellbore), a casing, a liner, a liner string, a hose, a mixer, a pump, a process facility, a storage vessel, a tanker, a railway tank car, a transport barge or ship, a separator, a contactor, a process vessel, and the like, any hybrid thereof, and any combination thereof. In cases where the flow path is a pipeline, or the like, the pipeline may be a pre-commissioned pipeline or an operational pipeline. It should be noted that the term "flow path" does not necessarily imply that a fluid is flowing therein, rather that a fluid is capable of being transported or otherwise flowable therethrough. In some embodiments, a flow path may be a component of a more complex system, for example, skids, trucks, pumps, and the like. In some embodiments, a flow path may comprise more than one section that is separated, but still fluidly communicable, by apparatuses like valves, flow meters, and the like.

As used herein, the term "electromagnetic radiation" refers to radio waves, microwave radiation, infrared and near-infrared radiation, visible light, ultraviolet light, X-ray radiation, and gamma ray radiation.

As used herein, the term "optical analysis device" refers to an optical device that is configured to receive an input of electromagnetic radiation from a substance or sample of the substance, produce output of electromagnetic radiation by interacting the input electromagnetic radiation with one or more chemical filters, and detect the output of electromagnetic radiation, which can be correlated to at least one characteristic of the substance being measured or monitored. The output of electromagnetic radiation from the one or more chemical filters can be reflected electromagnetic radiation, transmitted electromagnetic radiation, and/or dispersed electromagnetic radiation. Whether reflected or transmitted electromagnetic radiation is analyzed by the detector may be dictated by the structural parameters of the optical analysis device as well as other considerations known to those skilled in the art. In addition, emission and/or scattering by the substance, for example, via fluorescence, luminescence, Raman scattering, and/or Rayleigh scattering, can also be monitored by the optical analysis devices.

As used herein, the term "optically interact" or variations thereof refers to the reflection, transmission, scattering, diffraction, or absorption of electromagnetic radiation either on, through, or from one or more processing elements (i.e., integrated computational elements). Accordingly, optically interacted light refers to light that has been reflected, transmitted, scattered, diffracted, or absorbed by, emitted, or re-radiated, for example, using the integrated computational elements, but may also apply to interaction with a fluid or an analyte thereof.

The exemplary systems and methods described herein will include at least one optical analysis device arranged along or in a flow path in order to monitor a fluid or an analyte thereof flowing or otherwise contained within the flow path. Each optical analysis device may include an electromagnetic radiation source, at least one processing element (e.g., integrated computational element), and at least one detector arranged to receive optically interacted light from the at least one processing element. In some embodiments, the exemplary optical analysis devices may be specifically configured for detecting, analyzing, and quantitatively measuring a particular characteristic of interest in the flow path. In at least one embodiment, the characteristic may be related to a chemical process of interest (e.g., a cement setting process or carbonation corrosion) and the optical analysis devices may be configured to numerically determine the kinetics of reaction in near or real-time. In other embodiments, the optical analysis devices may be general purpose optical devices, with post-acquisition processing (e.g., through computer means) being used to specifically detect the characteristic of the fluid or an analyte thereof.

In some instances, an optical analysis device may be configured for optically interacting a sample, at least one chemical filter, and a detector. For example, an optical analysis device may, in some instances, include an electromagnetic radiation source arranged to optically interact light with a material of interest, at least one chemical filter arranged to receive the optically interacted light from the material of interest, and at least one detector arranged to receive the optically interacted light from the at least one chemical filter. However, in at least one embodiment, the electromagnetic radiation source may be omitted and instead the electromagnetic radiation may be derived from the material of interest itself.

In some embodiments, the exemplary optical analysis devices may be specifically configured for detecting, analyzing, and quantitatively measuring a particular characteristic of the material of interest. In other embodiments, the optical analysis devices may be general purpose optical devices, with post-acquisition processing (e.g., through computer means) being used to specifically detect the characteristic of interest.

The presently described optical analysis devices combine the advantage of the power, precision, and accuracy associated with laboratory spectrometers, while being extremely rugged and suitable for field use. Furthermore, the optical analysis devices can be specifically configured to detect and analyze particular characteristics of interest. As a result, interfering signals are automatically discriminated from those of interest by appropriate selection of the chemical filters, such that the optical analysis devices provide a rapid response regarding the characteristic of interest as based on the output from the detector and little post-processing is required. In some embodiments, the output from the detector can be converted into the magnitude of the characteristic of interest (e.g., the concentration of an analyte). The foregoing advantages and others make the optical analysis devices particularly well suited for field use.

The optical analysis devices described herein utilize electromagnetic radiation to mimic calculations, as opposed to the hardwired circuits of conventional electronic processors. When electromagnetic radiation interacts with a fluid or analyte thereof, unique physical and chemical information about the material of interest may be encoded in the electromagnetic radiation that is reflected from, transmitted through, or radiated therefrom. This information is often referred to as the spectral "fingerprint" of the material of interest. The optical analysis devices described herein are capable of extracting the information of the spectral fingerprint of multiple characteristics of a material of interest, e.g., a cement slurry, a spacer fluid, a treatment fluid, a drilling fluid, or an analyte thereof), and converting that information into a detectable output regarding the overall properties of the monitored material of interest. That is, through suitable configurations of the optical analysis devices, electromagnetic radiation associated with characteristics of interest in a fluid or analyte thereof can be separated from electromagnetic radiation associated with all other components of the fluid in order to estimate the properties of the monitored substance in real-time or near real-time.

The chemical filters described herein are generally a series of thin films that are deposited on a substrate. In some instances, the chemical filter may be deposited on the detector. In some instances, the chemical filter may be deposited on an optically transparent substrate (e.g., an IR-transparent substrate), which may be placed between the material of interest and the detector.

The chemical filters used in the exemplary optical analysis devices described herein selectively reduce the detector's sensitivity to wavelengths absorbed by the chemical filter. The pattern of the electromagnetic radiation intensities measured by the detector is similar to a mini-spectrum that contains only a few spectrally-convoluted measurements that are used as a basis for analysis. The chemical filters may be designed to either absorb the electromagnetic radiation having optically interacted with the material of interest or absorb the background electromagnetic radiation.

Referring now to FIG. 1, illustrated is an exemplary chemical filter 100 deposited on a detector 102 suitable for use in the optical analysis devices used in the systems and methods described herein. The chemical filter 100 includes a reflecting layer 104 between a sensing layer 106 and the detector 102.

The sensing layer 106 may enhance the sensitivity or selectivity of the detector. The sensing layer 106 may be formed by a thin film or series of thin films (e.g., thin films of polymers, complex organic molecules, semiconductors, and the like in any combination) where the thickness and composition of each thin film are used to produce a desired absorption characteristic. One of skill in the art would recognize the available techniques for designing and producing the sensing layer 106 of the chemical filter 100. For example, computer programs are available for designing the thickness and composition of the thin film or the series of thin films. Additionally, techniques like dip coating, sputter coating, and the like may be used for forming the thin films.

Accordingly, sensing layer 106 is configured to absorb at least a portion of an electromagnetic radiation interacting with chemical filter 100. In that regard, the electromagnetic radiation interacting with chemical filter 100 may be an electromagnetic radiation previously interacted with the sample (e.g., the dry cement). Moreover, sensing layer 106 may include a plurality of absorbing layers. Each absorbing layer in sensing layer 106 may be configured to absorb a different portion of the electromagnetic radiation interacted with the sample. For example, in some embodiments the accumulated absorption profiles of the plurality of absorbing layers forming sensing layer 106 may return an optical signal (i.e., absorption or transmission) of the sample when chemical filter 100 is interacted with an electromagnetic radiation. The thickness of each of the absorbing layers forming sensing layer 106 may be determined according to an optical thickness desired for sensing layer 106 in a portion of the spectrum of the electromagnetic radiation. The optical thickness desired for sensing layer 106 in a portion of the spectrum determines the amount of electromagnetic radiation absorbed and transmitted by chemical filter 100 in the portion of the spectrum. Thus, the number of absorbing layers, the material and the thickness of each of the absorbing layers result in an optical signal proportional to the characteristic of interest of the sample.

The reflecting layer 104 may act as an infrared mirror by reflecting wavelengths of non-interest. Gold, silver, and other interference coatings may be used to form the reflective layer 104. The reflective layer 104 may also enhance the thermal response of the detector 102 to wavelengths of interest.

In some instances, an absorbing layer may be used as an alternative to the reflecting layer 104, where the absorbing layer absorbs the wavelengths of non-interest.

In some instances, an insulating layer (not shown) may be included between the detector 102 and the chemical filter 100. The insulating layer may be deposited on the detector 102 before deposition of the various layers of the chemical filter 100, so as to prevent the detector 102 from shorting out during addition of the various layers of the chemical filter 100.

Detectors 102 suitable for use in conjunction with the optical analysis devices described herein may be thermal or charge coupled devices. Exemplary thermal devices may include thermocouples, thermopile arrays (thermocouples connected in series or parallel), bolometer detectors or microbolometer detectors (an array of pixels that measure a change in electrical resistance that occurs as a result of temperature change), and pyroelectric detectors (non-centrosymmetric crystalline materials that contain a dipole unit cell).

In embodiments where detector 102 is a thermal detector, reflecting layer 104 is configured to optically decouple detector 102 from the electromagnetic radiation interacted with the sample. Reflecting layer 104 may be formed of a material that thermally couples sensing layer 106 and detector 102. Accordingly, reflecting layer 104 may be configured to allow thermal energy to be transferred between sensing layer 106 and detector 102. Absorption of a portion of the electromagnetic radiation interacted with the sample in sensing layer 106 results in the heating of sensing layer 106. The heat of sensing layer 106 is transferred to and measured by thermal detector 102, thereby providing a signal indicative of the portion of the electromagnetic radiation interacted with the sample. When the electromagnetic radiation interacted with the sample is modulated at a certain frequency, fs, a thermal thickness, Tfs, above detector 102 defines the portion of chemical filter 100 that is thermally coupled with detector 102. Material layers located at a distance from detector 102 greater than Tfs may not be thermally coupled to detector 102. In some embodiments, Tfs varies inversely with frequency, fs. That is, a higher fs may result in a lower Tfs, according to some embodiments. Thus, by adjusting different values of fs, some embodiments are capable of determining an optical response of chemical filter 100 for each of a plurality of layers forming sensing layer 106.

As described above, in alternative embodiments, the detector 102 may be replaced with an optically transparent substrate to produce a chemical filter 100 that may be separate from the detector 102.

Figure 2:
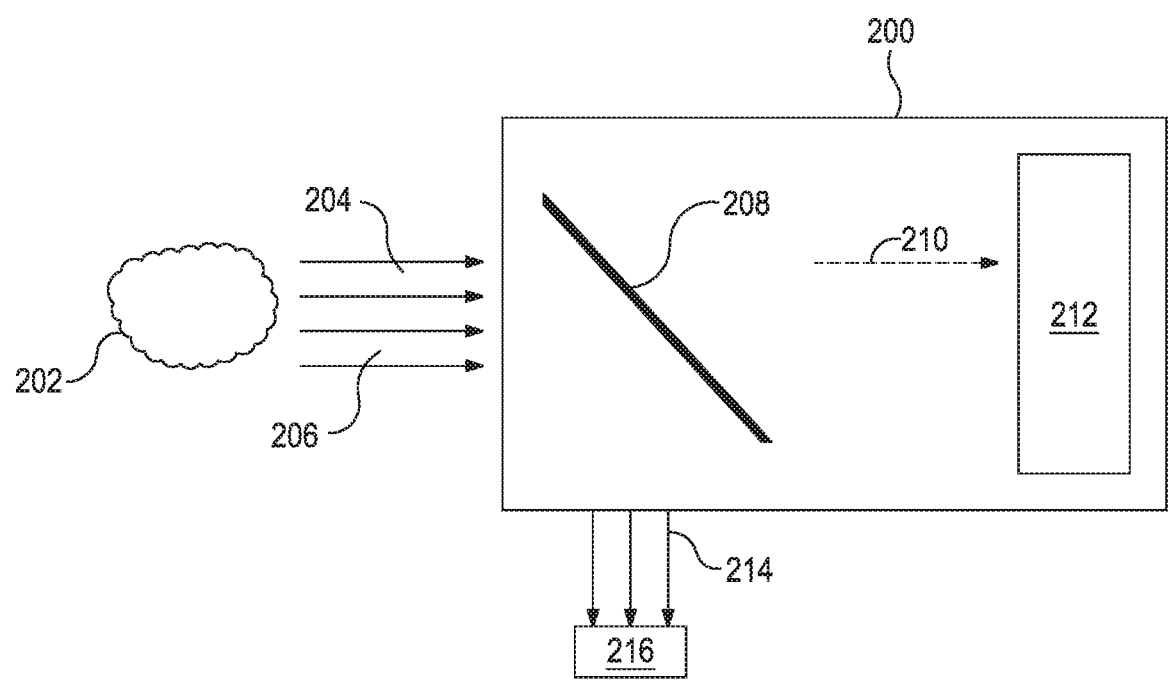
FIG. 2 illustrates a block diagram non-mechanistically illustrating how an optical analysis device distinguishes electromagnetic radiation related to a characteristic of interest from other electromagnetic radiation, according to one or more embodiments.

Referring now to FIG. 2, illustrated is a block diagram that non-mechanistically illustrates how an optical analysis device 200 is able to distinguish electromagnetic radiation related to a characteristic of interest from other electromagnetic radiation. As shown in FIG. 2, after being illuminated with incident electromagnetic radiation, a material of interest 202 (e.g., a fluid or a set cement) produces an output of electromagnetic radiation (e.g., sample-interacted light), some of which is electromagnetic radiation 204 corresponding to the characteristic of interest and some of which is background electromagnetic radiation 206 corresponding to other characteristics of the material of interest 202. In some embodiments, the material of interest 202 may include one or more characteristics of interest that may correspond to the one or more analytes of the material of interest 202.

Although not specifically shown, one or more conventional filters may be employed in the optical analysis device 200 in order to restrict the optical wavelengths and/or bandwidths of the system and thereby eliminate unwanted electromagnetic radiation existing in wavelength regions that have no importance. Such filters can be located anywhere along the optical train, but are typically employed directly after a light source, which provides the initial electromagnetic radiation.

The beams of electromagnetic radiation 204, 206 impinge upon the optical analysis device 200, which contains an exemplary chemical filter 208 therein. In the illustrated embodiment, the chemical filter 208 may be configured to produce optically interacted light, for example, transmitted optically interacted light 210 and reflected optically interacted light 214 (e.g., where the chemical filter 208 includes a reflecting layer described relative to FIG. 1). In operation, the chemical filter 208 may be configured to distinguish the electromagnetic radiation 204 from the background electromagnetic radiation 206 as described relative to FIG. 1.

The transmitted optically interacted light 210, which may be related to the characteristic of interest of the material of interest 202, may be conveyed to a detector 212 for analysis and quantification. As illustrated, the chemical filter 208 may be separate from the detector 212.

In embodiments where detector 212 is a thermal detector, chemical filter 208 may be thermally coupled to the sensitive area of detector 212. For example, in some embodiments chemical filter 208 includes a sensing layer adjacent to detector 212 (e.g., chemical filter 100, cf. FIG. 1).

In some embodiments, the detector 212 is configured to produce an output signal in the form of a voltage that corresponds to the particular characteristic of the material of interest 202. In at least one embodiment, the signal produced by the detector 212 and the characteristic of a material of interest 202 (e.g., concentration of an analyte) may be directly proportional. In other embodiments, the relationship may be a polynomial function, an exponential function, and/or a logarithmic function. The reflected optically interacted light 214, which may be related to other characteristics of the material of interest 202, can be directed away from detector 212. In alternative configurations, the chemical filter 208 may be configured such that the reflected optically interacted light 214 can be related to the characteristic of interest, and the transmitted optically interacted light 210 can be related to other characteristics in the material of interest 202. In alternative configuration, the chemical filter 208 may include an absorbing layer rather than a reflecting layer, thereby absorbing the optically interacted light corresponding to the background such that the transmitted optically interacted light 210 is related to other characteristics of the material of interest 202.

In some embodiments, a second detector 216 can be present and arranged to detect the reflected optically interacted light 214. In other embodiments, the second detector 216 may be arranged to detect the electromagnetic radiation 204,206 derived from the material of interest 202 or electromagnetic radiation directed toward or before the material of interest 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical analysis device 200, combinations thereof, or the like. In some embodiments, a beam splitter (not shown) can be employed to split the electromagnetic radiation 204,206, and the transmitted or reflected electromagnetic radiation can then be directed to two or more chemical filters 208. That is, in such embodiments, the chemical filter 208 does not function as a type of beam splitter, as depicted in FIG. 2, and the transmitted or reflected electromagnetic radiation simply passes through the chemical filter 208, being optically interacted therein, before travelling to the detector 212.

The characteristic(s) of interest being analyzed using the optical analysis device 200 can be further processed and/or analyzed computationally to provide additional characterization information about the material of interest 202 or an analyte thereof. In some embodiments, the identification and concentration of each analyte of interest in the material of interest 202 can be used to predict certain physical characteristics of the material of interest 202. For example, the bulk characteristics of the material of interest 202 (e.g., reactivity, set time, amount of corrosion, and the like) can be estimated by using a combination of the properties conferred to the material of interest 202 by each analyte.

In some embodiments, the concentration or magnitude of the characteristic of interest determined using the optical analysis device 200 can be fed into an algorithm operating under computer control. The algorithm may be configured to make predictions on how the characteristics of the material of interest 202 would change if the magnitude of the characteristic of interest are changed relative to one another. In some embodiments, the algorithm can produce an output that is readable by an operator who can manually take appropriate action, if needed, based upon the reported output. In other embodiments, however, the algorithm can take proactive process control by, for example, automatically adjusting the flow of a fluid being introduced into a flow path or by halting the introduction of the fluid in response to an out of range condition, for example, if premature setting is detected.

In some embodiments, the characteristics of interest determined using the optical analysis devices 200 can be associated with a timestamp. A timestamp may be useful in reviewing and analyzing the history of the characteristic of interest, which may be of added value in building a library of cement setting processes or cement corrosion processes. In some embodiments, the characteristics of interest, optionally timestamped, can be fed into an algorithm operating under computer control. The algorithm may be configured to make predictions on the status of the cement setting process (or cement corrosion processes) and/or any operational parameters that need to be changed as described further below. In some embodiments, the algorithm can produce an output that is readable by an operator who can manually take appropriate action, like initiation of a remedial operation, if needed, based upon the output.

The algorithm can be part of an artificial neural network configured to use the concentration of each characteristic of interest in order to evaluate the overall characteristic(s) of the material of interest 202 and predict the composition and/or concentration of the cement slurry additives to be included to provide for desired properties in a resultant cement slurry. It is to be recognized that an artificial neural network can be trained using samples of predetermined characteristics of interest, and thereby generating a virtual library. As the virtual library available to the artificial neural network becomes larger, the neural network can become more capable of accurately predicting the characteristic of interest corresponding to a fluid or analyte thereof. Furthermore, with sufficient training, the artificial neural network can more accurately predict the characteristics of the fluid, even in the presence of unknown analytes.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical analysis devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a chemical reaction process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site (e.g., via wireless technology).

Figure 3:
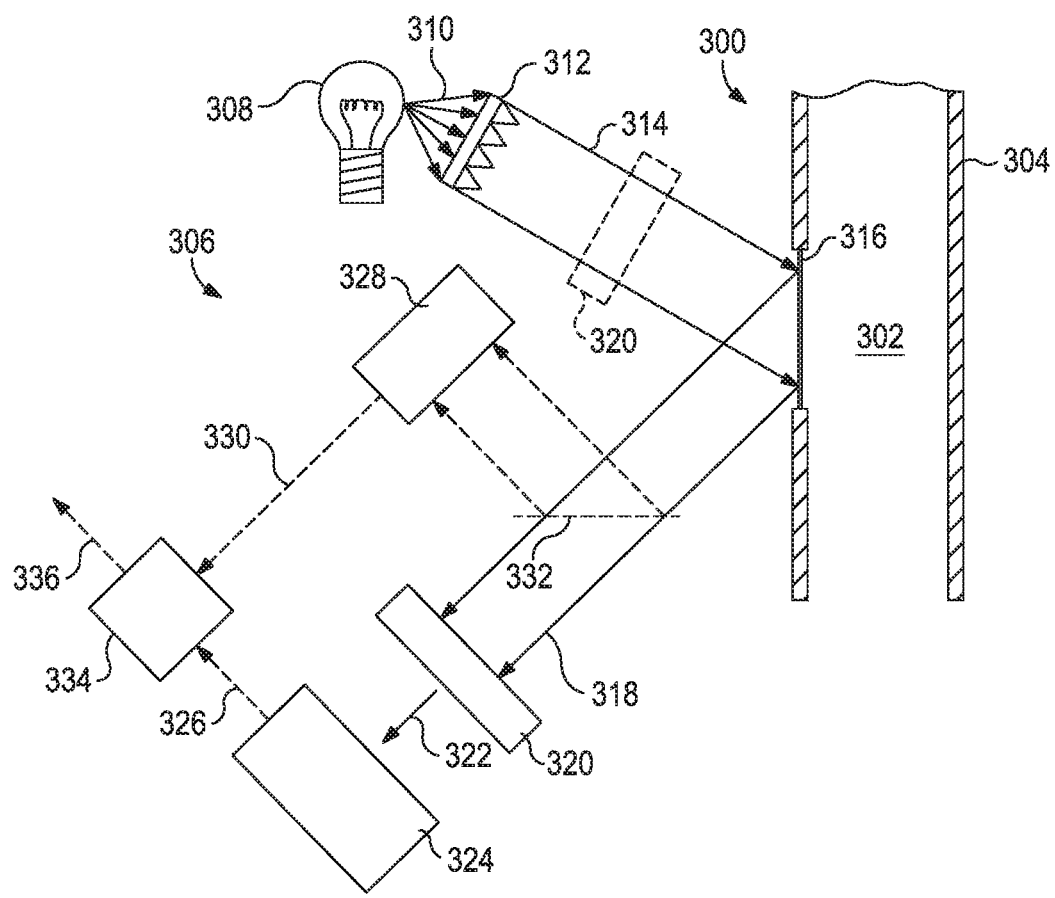
FIG. 3 illustrates an exemplary system for monitoring a material of interest present in a flow path, according to one or more embodiments.

Referring now to FIG. 3, illustrated is an exemplary system 300 for monitoring a material of interest 302, according to one or more embodiments. In the illustrated embodiment, the material of interest 302 may be contained within an exemplary flow path 304. In at least one embodiment, the flow path 304 may be a wellbore and the material of interest 302 present therein may be actively flowing while measurements are being taken. In at least one embodiment, the flow path 304 may be a cup, or the like, of a mobile device. As will be appreciated, however, in other embodiments the flow path 304 may be any other type of container, as generally described or otherwise defined herein. For example, the flow path 304 may be the interior of a casing or the annulus between a casing and the wellbore.

The system 300 may include at least one optical analysis device 306, which may be similar in some respects to the optical analysis device 200 of FIG. 2, and therefore may be best understood with reference thereto. While not shown, the device 306 may be housed within a casing or housing configured to substantially protect the internal components of the device 306 from damage or contamination from the external environment. The housing may operate to mechanically couple the device 306 to the flow path 304 with, for example, mechanical fasteners, brazing or welding techniques, adhesives, magnets, combinations thereof, or the like.

As described in greater detail below, the optical analysis device 306 may be useful in determining a particular characteristic of the material of interest 302 so as to identify the material of interest 302 within the flow path 304, which may be correlated to the location of the optical analysis device 306 along the flow path 304.

In some embodiments, the device 306 may include an electromagnetic radiation source 308 (e.g., a broadband light source) configured to emit or otherwise generate electromagnetic radiation 310. The electromagnetic radiation source 308 may be any device capable of emitting or generating electromagnetic radiation, as defined herein. For example, the electromagnetic radiation source 308 may be a light bulb, a light emitting device (LED), a laser, a blackbody, a photonic crystal, an X-Ray source, combinations thereof, or the like. In some instances, the electromagnetic radiation source 308 may be modulated such that the frequency of electromagnetic radiation incident on the sample, fs, changes. This may be achieved with a filter wheel, an optical chopper, optical choppers, and the like. Accordingly, in some embodiments different values of fs may be used during a measurement cycle. Moreover, in some embodiments the value of fs may be adjusted continuously in order to collect signals from different sensing layers in a chemical filter 320. By changing the modulation frequency, fs, the thermal diffusion length, Ts, is also changed. Ts determines the amount of time the electromagnetic radiation spends in a particular layer; therefore, by modifying or adjusting fs accordingly, one can effectively activate or deactivate different sensing layers. For example, the fs could be chosen to make all layers thermally thin. In this case, all layers would be inside of Ts and the detected optical signal would be the result of absorption by all layers. In yet another example, fs could be selected so that only the sensing layers close to the detector are thermally thin and all other layers are outside of Ts. The detected optical signal in this example would be the result of absorption in only those layers close to the detector or inside of Ts. In some embodiments, a lens 312 may be configured to collect or otherwise receive the electromagnetic radiation 310 and direct a beam 314 of electromagnetic radiation 310 toward the material of interest 302. The lens 312 may be any type of optical device configured to transmit or otherwise convey the electromagnetic radiation 310 as desired. For example, the lens 312 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 312 may be omitted from the device 306 and the electromagnetic radiation 310 may instead be conveyed toward the material of interest 302 directly from the electromagnetic radiation source 308.

In one or more embodiments, the device 306 may also include a sampling window 316 arranged adjacent to or otherwise in contact with the material of interest 302 for detection purposes. The sampling window 316 may be made from a variety of transparent, rigid or semi-rigid materials that are configured to allow transmission of the electromagnetic radiation 310 therethrough. For example, the sampling window 316 may be made of, but is not limited to, glasses, plastics, semi-conductors, crystalline materials, polycrystalline materials, hot or cold-pressed powders, combinations thereof, or the like.

After passing through the sampling window 316, the electromagnetic radiation 310 impinges upon and optically interacts with the material of interest 302, including any analytes present within the material of interest 302. As a result, optically interacted radiation 318 is generated by and reflected from the material of interest 302. Those skilled in the art, however, will readily recognize that alternative variations of the device 306 may allow the optically interacted radiation 318 to be generated by being transmitted, scattered, diffracted, absorbed, emitted, or re-radiated by and/or from the material of interest 302, or one or more analytes present within the material of interest 302, without departing from the scope of the disclosure.

The optically interacted radiation 318 generated by the interaction with the material of interest 302 may be directed to or otherwise received by a chemical filter 320 arranged within the device 306. In operation, the chemical filter 320 may be configured to receive the optically interacted radiation 318 and produce modified electromagnetic radiation 322 corresponding to a particular characteristic of interest of the material of interest 302. In particular, the modified electromagnetic radiation 322 is electromagnetic radiation that has optically interacted with the chemical filter 320, whereby an approximate mimicking of the absorption spectrum corresponding to the characteristic of interest is obtained. In some embodiments, the characteristic of interest corresponds to the material of interest 302. In other embodiments, the characteristic of interest corresponds to a particular analyte found in the material of interest 302.

It should be noted that, while FIG. 3 depicts the chemical filter 320 as receiving optically interacted radiation 318 from the material of interest 302, the chemical filter 320 may be arranged at any point along the optical train of the device 306, without departing from the scope of the disclosure. For example, in one or more embodiments, the chemical filter 320 (as shown in dashed) may be arranged within the optical train prior to the sampling window 316 and equally obtain substantially the same results. In other embodiments, the sampling window 316 may serve a dual purpose as both a transmission window and the chemical filter 320 (i.e., a spectral component). In yet other embodiments, the chemical filter 320 may generate the modified electromagnetic radiation 322 through reflection, instead of transmission therethrough. In further embodiments, chemical filter 320 may include a sensing layer disposed adjacent to a thermal detector (e.g., chemical filter 100 and detector 102, cf. FIG. 1), the sensing layer modifying an electromagnetic radiation optically interacted with dry cement 302.

Moreover, while only one chemical filter 320 is shown in the device 306, embodiments are contemplated herein which include the use of at least two chemical filters 320 or components thereof in the device 306 configured to cooperatively determine the characteristic of interest in the material of interest 302. For example, two or more chemical filters 320 may be arranged in series or parallel within the device 306 and configured to receive the optically interacted radiation 318 and thereby enhance sensitivities and detector limits of the device 306. In other embodiments, two or more chemical filters 320 may be arranged on a movable assembly, such as a rotating disc or an oscillating linear array, which moves such that the individual chemical filter 320 or components thereof are able to be exposed to or otherwise optically interact with electromagnetic radiation 310 for a distinct brief period of time. The two or more chemical filters 320 or components thereof in any of these embodiments may be configured to be either associated or disassociated with the characteristic of interest in the material of interest 302.

In some embodiments, it may be desirable to monitor more than one characteristic of interest at a time using the device 306. In such embodiments, various configurations for multiple chemical filters 320 can be used, where each chemical filter 320 is configured to detect a particular and/or distinct characteristic of interest corresponding, for example, to the material of interest 302 or an analyte in the material of interest 302. In some embodiments, the characteristic of interest can be analyzed sequentially using multiple chemical filters 320 that are provided a single beam of optically interacted radiation 318 being reflected from or transmitted through the material of interest 302. In some embodiments, as briefly mentioned above, multiple chemical filters 320 can be arranged on a rotating disc, where the individual chemical filters 320 are only exposed to the beam of optically interacted radiation 318 for a short time. Advantages of this approach can include the ability to analyze multiple characteristics of interest within the material of interest 302 using a single device 306 and the opportunity to assay additional characteristics simply by adding additional chemical filters 320 to the rotating disc corresponding to those additional characteristics.

In other embodiments, multiple devices 306 can be placed at a single location along the flow path 304, where each device 306 contains a unique chemical filter 320 that is configured to detect a particular characteristic of interest. In such embodiments, a beam splitter can divert a portion of the optically interacted radiation 318 being reflected by, emitted from, or transmitted through the material of interest 302 and into each device 306. Each device 306, in turn, can be coupled to a corresponding detector (e.g., detector 324) or detector array that is configured to detect and analyze an output of electromagnetic radiation from the respective optical analysis device. Parallel configurations of optical analysis devices can be particularly beneficial for applications that require low power inputs and/or no moving parts.

Those skilled in the art will appreciate that any of the foregoing configurations can further be used in combination with a series configuration in any of the present embodiments. For example, two devices 306 may be arranged in series, such as being located on or within a movable housing configured to perform an analysis at a single location in the flow path 304. Likewise, multiple detection stations, each containing devices 306 in parallel, can be placed in series for performing a similar analysis.

The modified electromagnetic radiation 322 generated by the chemical filter 320 may subsequently be conveyed to a detector 324 for quantification of the signal. The detector 324 may be any device capable of detecting electromagnetic radiation, and may be generally characterized as an optical transducer. In some embodiments, the detector 324 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 324 may be configured to produce an output signal 326 in real-time or near real-time in the form of a voltage (or current) that corresponds to the particular characteristic of interest in the material of interest 302. The voltage returned by the detector 324 is essentially the dot product of the optical interaction of the optically interacted radiation 318 with the respective chemical filter 320 as a function of the concentration of the characteristic of interest. As such, the output signal 326 produced by the detector 324 and the concentration of the characteristic of interest may be related, for example, directly proportional. In other embodiments, however, the relationship may correspond to a polynomial function, an exponential function, a logarithmic function, and/or a combination thereof.

In some embodiments, the device 306 may include a second detector 328 which may be similar to the first detector 324 in that it may be any device capable of detecting electromagnetic radiation. Similar to the second detector 216 of FIG. 2, the second detector 328 of FIG. 3 may be used to detect radiating deviations stemming from the electromagnetic radiation source 308. Undesirable radiating deviations can occur in the intensity of the electromagnetic radiation 310 due to a wide variety of reasons and potentially causing various negative effects on the output of the device 306. These negative effects can be particularly detrimental for measurements taken over a period of time. In some embodiments, radiating deviations can occur as a result of a build-up of film or material on the sampling window 316 which has the effect of reducing the amount and quality of light ultimately reaching the first detector 324. Without proper compensation, such radiating deviations could result in false readings and the output signal 326 would no longer be primarily or accurately related to the characteristic of interest.

To compensate for these types of undesirable effects, the second detector 328 may be configured to generate a compensating signal 330 generally indicative of the radiating deviations of the electromagnetic radiation source 308, and thereby normalize the output signal 326 generated by the first detector 324. As illustrated, the second detector 328 may be configured to receive a portion of the optically interacted radiation 318 via a beam splitter 332 in order to detect the radiating deviations. In other embodiments, however, the second detector 328 may be arranged to receive electromagnetic radiation from any portion of the optical train in the device 306 in order to detect the radiating deviations, without departing from the scope of the disclosure.

In some applications, the output signal 326 and the compensating signal 330 may be conveyed to or otherwise received by a signal processor 334 communicably coupled to both the detectors 324, 328. The signal processor 334 may be a computer including a non-transitory machine-readable medium, and may be configured to computationally combine the compensating signal 330 with the output signal 326 in order to normalize the output signal 326 in view of any radiating deviations detected by the second detector 328. In some embodiments, computationally combining the output and compensating signals 326, 330 may entail computing a ratio of the two signals 326, 330. For example, the concentration or magnitude of each characteristic of interest determined using the optical analysis device 306 can be fed into an algorithm run by the signal processor 334.

In real-time or near real-time, the signal processor 334 may be configured to provide a resulting output signal 336 corresponding to the characteristic of interest, such as a concentration of a reagent or resulting product present in the fluid. In some embodiments, as briefly discussed above, the resulting output signal 336 may be readable by an operator who can consider the results and make proper adjustments to the flow path or take appropriate action, if needed, based upon the magnitude of the measured characteristic of interest. In some embodiments, the resulting output signal 336 may be conveyed, either wired or wirelessly, to the user for consideration.

Figure 4:
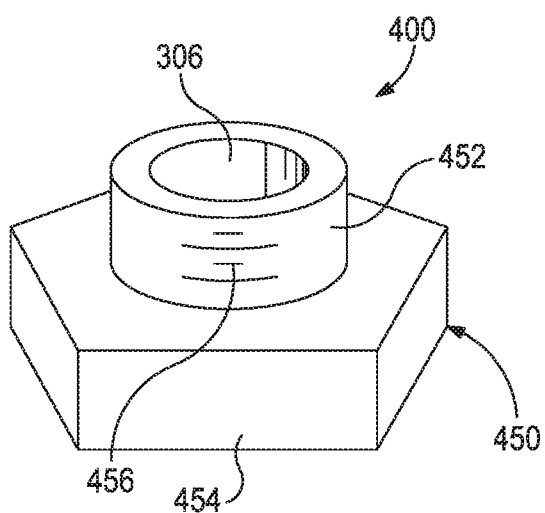
FIG. 4 illustrates an exemplary housing that may be used to house an optical analysis device, according to one or more embodiments.

Referring now to FIG. 4, with continued reference to FIG. 3, illustrated is an exemplary housing 400 that may be used to house an optical analysis device, according to one or more embodiments. In some embodiments, the housing 400 may be mechanically coupled to the flow path 304 using, for example, mechanical fasteners, brazing or welding techniques, adhesives, magnets, combinations thereof or the like. The housing 400 may be configured to substantially protect the internal components of the respective device 306 from damage or contamination from the external environment. Those skilled in the art, however, will readily recognize that several alternative designs and configurations of housings used to house the optical analysis devices are suitable for the presently disclosed systems and methods. Indeed, the housing embodiments described and disclosed herein are by way of example only, and should not be considered limiting to the exemplary systems and methods disclosed herein.

As illustrated, the housing 400 may be in the general form of a bolt 450 which encloses the various components of an optical analysis device, such as the device 306 of FIG. 3. In one embodiment, the components of the device 306 housed within the housing 400 may be generally housed within a stem 452 of the bolt 450, and the bolt 450 may have a hex head 454 for manual manipulation of the housing 400 using, for example, a wrench or other suitable torque-generating hand tool.

In at least one embodiment, the housing 400 defines external threads 456 that are threadable with corresponding mating pipe threads provided in, for example, an opening defined in the flow path 304 (FIG. 3) that is configured to receive the housing 400. The threads 456 may be sealed to the mating pipe threads with a thread sealant. The sampling window 316 is configured to be in optical communication with the material of interest 302 (FIG. 3) and allows optical interaction between the material of interest 302 and the other internal components of the internally-housed device 306.

Systems with optical analytical devices and housings for containing the systems similar to that illustrated in FIGS. 2-4 may be useful in analyzing fluids described herein or set cements. For example, the optical analytical device and corresponding hardware (e.g., lenses, housings, light sources, and the like) may be fastened or integral to a casing, a centralizer, or other suitable wellbore tool that would contact the various fluids introduced into a wellbore during cementing operations. For embodiments used in detecting carbonation corrosion of a set cement, the optical analytical device and corresponding hardware may be fastened or integral to the casing. In another example, the optical analytical device and corresponding hardware may be placed in the fluids being pumped where a radio frequency or other tracking means is included to identify the location of the optical analytical device. For example, a dart or perf ball may include an optical analytical device described herein, where operation in reflection mode (i.e., electromagnetic radiation from the optical analytical device interacts with the material of interest and reflected, interacted electromagnetic radiation is measured and analyzed by the optical analytical device). Additionally, the chemical filter may preferably be coupled to the detector because the amount of reflected light is often a low percentage of the optical signal. Alternatively, diffuse reflection with a short path length would allow for use of a chemical filter decoupled from the detector.

Figure 5:
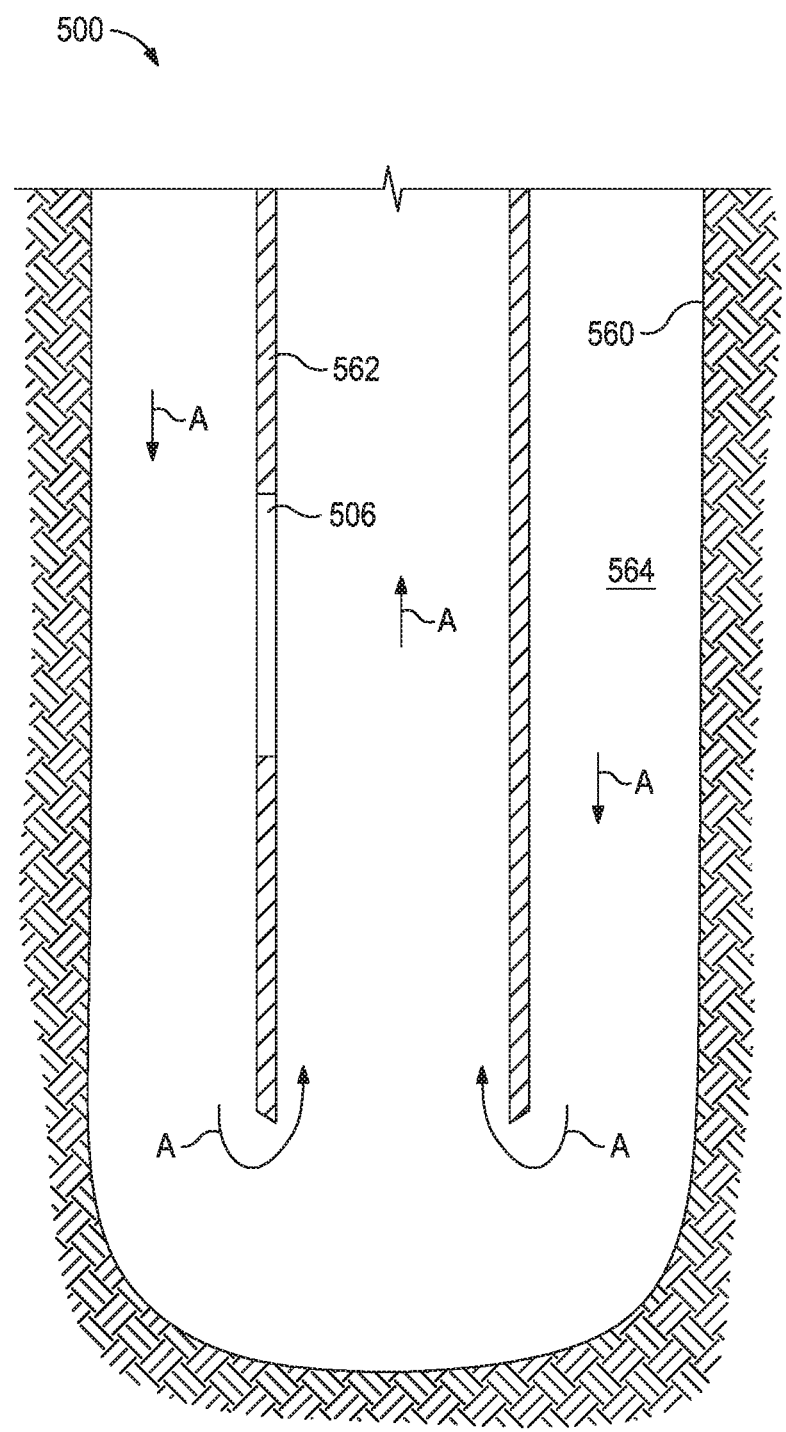
FIG. 5 illustrates an exemplary system for monitoring a material of interest, according to one or more embodiments.

Referring now to FIG. 5, illustrated is an exemplary system 500 for monitoring a fluid, such as a chemical reaction process that may occur within the fluid and/or to ascertain the location of the fluid, according to one or more embodiments. In the illustrated embodiment, the fluid may be contained within or otherwise flowing through an exemplary flow path provided by the casing 562 and/or an annulus 564 defined between the wellbore 560 and the casing 562. In at least one embodiment, the fluid present therein may be flowing in the general direction indicated by the arrows A (e.g., in a reverse cementing operation). As will be appreciated, however, in other embodiments the flow path may be any other type of flow path, as generally described or otherwise defined herein. For example, the flow path may be a storage or reaction vessel and the fluid may not necessarily be flowing while being monitored.

The system 500 may include at least one optical analysis device 306, which may be similar in some respects to the optical analysis device 200 of FIG. 2, and therefore may be best understood with reference thereto. The optical analysis device 506 may be housed within a casing or housing (not shown) configured to substantially protect the internal components of the device 506 from damage or contamination from the external environment. The housing may operate to mechanically couple the device 506 to the casing 562 with, for example, mechanical fasteners, brazing or welding techniques, adhesives, magnets, combinations thereof and the like. In operation, the housing may be designed to withstand the pressures that may be experienced within or without the flow path and thereby provide a fluid tight seal against external contamination.

As described in greater detail below, the optical analysis device 506 may be useful in determining a particular characteristic of the fluid within the flow path, such as determining a concentration of an analyte (e.g., reagent or product) present within the fluid. In the event the fluid is a cement slurry, knowing the presence and/or concentration of analytes found in the cement slurry may help determine, in some embodiments, (1) the location of the cement slurry (e.g., by monitoring a spacer fluid and/or the cement slurry) and/or (2) the status of the cement setting processes of the cement slurry. Knowing any one of the foregoing may provide guidance to an operator as to parameters of the current operation or subsequent operations. For example, knowing the location of the cement slurry may be useful in determining appropriate pumping speeds of the cement slurry. In other instances, knowing the precise location of the cement slurry as opposed to a generalized calculation of its location (i.e., the location of the cement slurry calculated using, inter alia, the amount of cement slurry introduced, the flow rate, and the estimated volume to be filled) may be used to determine if the amount of cement slurry used in a particular cementing operation should be changed so as to prevent an unnecessary second cementing operation if too little is used. An accurate determination of the location of the cement slurry may also forego the need for remedial operations (e.g., drill-out operations) in the event too much cement slurry is used. In yet other instances, comparing the location of the cement slurry to its calculated location may be useful in determining if damage has occurred to a wellbore, for example, where cement may be leaking or lost into, and perhaps damaging, the adjacent subterranean formation. In other instances, comparing the actual location of the cement slurry to the calculated location may avert losing fluids to the formations by identifying presence of potential thief zones (i.e., natural or man-made high permeability zones such as fractures, vugular zones, or voids) into which large volumes (e.g., <10 to >500 barrels of fluid per hour) of a fluid can be lost. Further, in some reverse cementing operation embodiments, knowing the time of arrival of a cement slurry at the bottom of the casing may be advantageous for preventing entry of an excessive amount cement slurry into the pipe that will require a remedial operation, e.g., a drillout.

In some instances, the device 506 may be an integral part of the casing 562. One skilled in the art would understand that the device 506 may be coupled to the casing 562 so as to be disposed on a surface of the casing 562, partially integrated into a wall of the casing 562, extended outwardly beyond a surface of the casing 562, be flush with a surface of the casing 562, and any hybrid thereof. In some embodiments, the device 506 may be coupled to the casing 562 so as to monitor a fluid in the annulus 564 and/or a fluid in the casing 562.

As described above, the information regarding the characteristic of interest may be conveyed wired (e.g., via fiber optics) and/or wirelessly to an operator or computer program that may take an appropriate action, if needed. For example, if a lost circulation zone is identified, additional cement slurry may need to be introduced into the wellbore to account for the lost slurry. In another example, if the cement slurry appears to be setting more rapidly than expected, a flow rate may be increased to place the cement slurry in the appropriate place downhole before becoming unpumpable.

Figure 6:
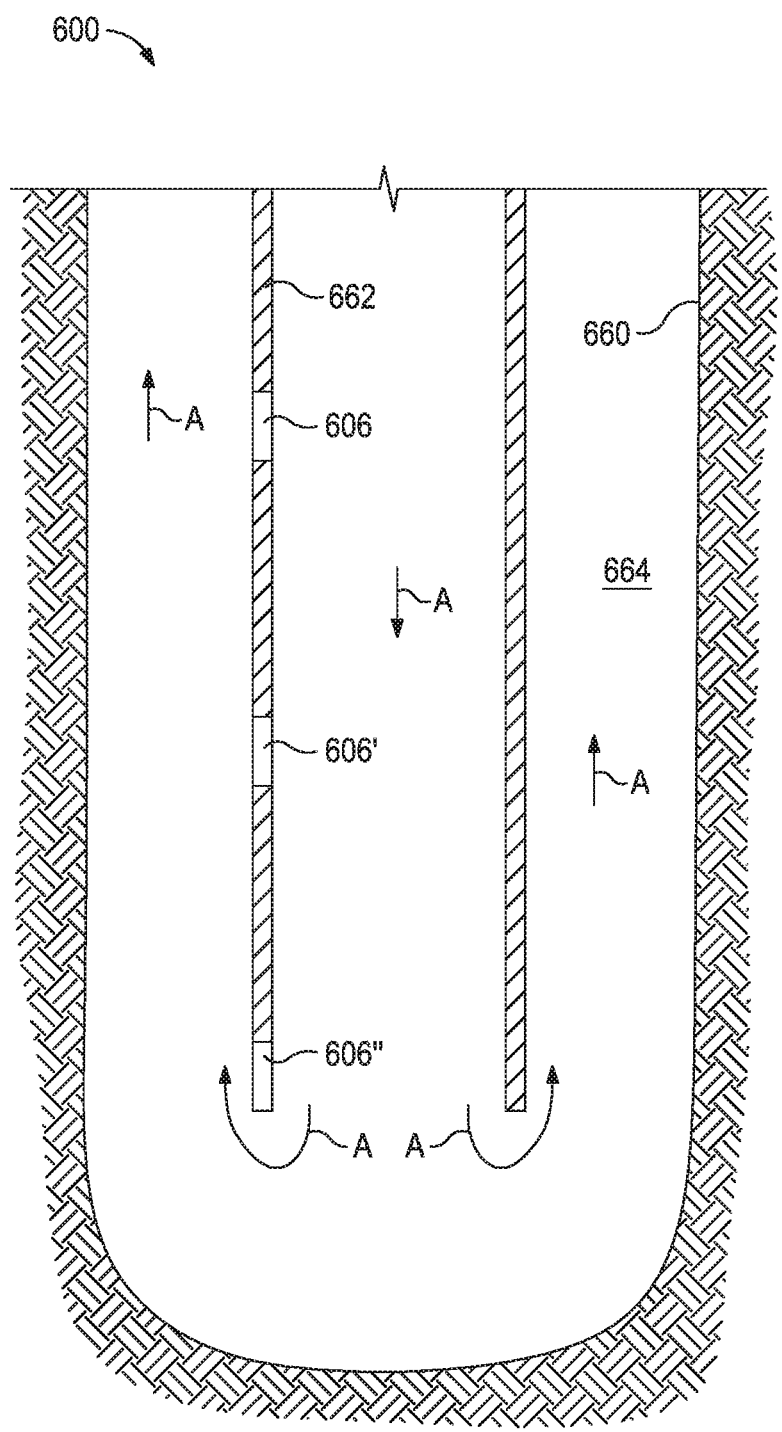
FIG. 6 illustrates another exemplary system for monitoring a material of interest, according to one or more embodiments.

Referring now to FIG. 6, illustrated is an exemplary system 600 for monitoring a fluid according to one or more embodiments. In the illustrated embodiment, the system 600 includes a plurality of optical analysis devices 606,606',606" coupled to a casing 662 in series along the length of the casing 662. Each optical analysis device 606,606',606" may be similar to the optical analysis device 306 of FIG. 3 or any of the alternate embodiments described herein, and therefore will not be described again in detail. Such a plurality of devices 606,606',606" may be advantageous to monitor the location and status of fluids during a wellbore operation. For example, illustrated in FIG. 6 is a traditional cementing operation for completing a wellbore 660. As illustrated by arrows A, a fluid (i.e., cement slurry) may flow through the casing 662 change directions at the end of a casing 662 so as to flow through the annulus 664 defined between the wellbore 660 and the casing 662.

As illustrated in FIG. 6, a first device 606" may be disposed at the end of the casing 662 where the fluid enters the annulus 664. Arranging the first device 606" at such a location may be advantageous in determining when the fluid has reached the end of the casing 662. Second and third devices 606 and 606' may be useful in monitoring the location of the fluid as it moves through the annulus 664 and/or the casing 662. In some instances, calculating the actual speed with which the fluid moves through the annulus 664 and/or the casing 662 with the devices 606,606',606" may be compared to the calculated speed the fluid should be moving. A slow actual speed may be an indicator that the fluid is being lost into portions of the subterranean formation. Knowing fluid loss is occurring at some point in the wellbore 660 may allow for the operator to change the pumping speeds to minimize fluid loss, or otherwise add additional fluid to the operation to ensure complete and proper placement of a cement slurry. A determination of fluid loss in the wellbore 660 may also provide the operator with an opportunity to proactively alter the properties and/or composition of the fluid being pumped into the wellbore, such as by adding fluid loss control agents, to minimize fluid loss.

As with the embodiments discussed above, the devices 606,606',606" may independently include multiple chemical filters and be configured to measure one or more characteristics of the fluid in the annulus 664 and the casing 662. Those skilled in the art will readily appreciate the various and numerous applications that the systems 500 and 600, and alternative configurations thereof, may be suitably used with.

In a cementing operation, a fluid or series of fluids (i.e., two or more fluids in series) may be introduced into a wellbore or an annulus defined therein. The fluid or series of fluids may optically interact with at least one chemical filter described herein and at least one detector described herein of at least one optical analytical device described herein. The chemical filters/detectors may be configured to detect at least one characteristic of interest of the fluid or series of fluids. The detector may then generate an output signal corresponding to the characteristics of the fluid or series of fluids. At least one signal processor may then receive and process the output signals to produce a value for each of the characteristics measured and analyzed. In some instances, these values may then be used to identify the fluid or series of fluids. In some instances, these values may then be used to the status of the cement setting process. In some instances, the location of the optical analytical device may be correlated to one of the foregoing.

The fluid or series of fluids used during a cementing operation may include a cement slurry, a spacer fluid, a flush fluid, a displacement fluid, or any combination thereof.

A cement slurry may, in some embodiments, comprise an aqueous fluid, cement particles, and optionally further comprise fillers and/or additives like set-time modifiers and other analytes listed herein. In some embodiments, a cement slurry may be foamed and comprise an aqueous fluid, cement particles, a gas, and a foaming agent and optionally further comprise fillers and/or additives like set-time modifiers and other analytes listed above. In alternative embodiments, the cement slurry may be a settable fluid that does not include cement particles as described herein (e.g., being a latex settable fluid).

A spacer fluid is generally a smaller volume of fluid disposed between two other fluids to mitigate mixing of the two other fluids. In some embodiments, a spacer fluid may comprise an aqueous fluid, a weighting agent, surfactants, and optionally further comprise additives like salts and other analytes listed above.

A flush fluid is generally a fluid used at the beginning of a cementing operation to flush a fluid contained in the wellbore (e.g., a drilling fluid or a treatment fluid). In some embodiments, a flush fluid may comprise an aqueous fluid, a weighting agent, surfactants, and optionally further comprise additives like salts and other analytes listed above.

A displacement fluid is generally a fluid used at the end of a cementing operation to displace a sufficient amount of cement slurry to place the cement slurry in the desired location in the wellbore. In some embodiments, a displacement fluid may comprise an aqueous fluid, a weighting agent, surfactants, and optionally further comprise additives like salts and other analytes listed above.

The fluid or series of fluids may include one or more of the foregoing fluids. For example, in some embodiments, a cement slurry may be introduced after a drilling fluid optionally with a spacer fluid therebetween. In some instances, the cement slurry may be followed by a displacement fluid optionally with a spacer fluid therebetween.

As described herein, the optical analysis devices described herein may be used to identify or distinguish between each of the fluids. In some embodiments, at least one fluid used in the cementing operation may comprise a tracer additive having the primary function of being detected by a device comprising the integrated computational element.

In some instances, when two or more optical analysis devices are implemented along a flow path, the actual location of the fluid can be compared to the predicted location. When the two locations are inconsistent, remedial actions may be taken where a parameter of the wellbore operation may be changed. For example, more cement slurry may be introduced to account for a potential lost circulation zone. Alternatively, the fluid being introduced may be changed to a remedial pill (i.e., a small volume of a remedial fluid) designed to plug the lost circulation zone before resuming the cementing operations. Also, a displacement fluid may be introduced to allow for other remedial actions to plug or isolate the lost circulation zone.

When the identity of the fluid is correlated to a location of the optical analysis device, the position of the fluid or progress of the cementing operation may be monitored. Additionally, when analyzing the cement slurry, the characteristics of interest measured by the optical analysis device may be related to the status of the cement setting process. If the cement setting process is further along than expected, a parameter of the wellbore operation (e.g., pumping speed) may be changed to move the cement slurry more quickly to the desired location along the flow path. In some embodiments, knowing the status of a cement setting process may be used for, inter alia, determining the timing of a subsequent subterranean operation. Performing an operation before the cement has set may cause damage to the cement and necessitate costly remedial operations. In situ monitoring of cement setting processes may eliminate the need for costly and time-consuming wireline logging operations. Further, in situ monitoring may further reduce the time between the cementing operation and a subsequent operation, in that, the cement may set more quickly than expected and in situ monitoring would provide real-time or near real-time data to that effect.

In some instances, after the cement has set, appropriately configured optical analysis devices may then be used to analyze the set cement. The set cement may optically interact with at least one chemical filter described herein and at least one detector described herein of at least one optical analytical device described herein. The chemical filters/detectors may be configured to detect at least one characteristic of interest of the set cement. The detector may then generate an output signal corresponding to each of the characteristics of the set cement. At least one signal processor may then receive and process the output signals to produce a value for each of the characteristics measured and analyzed. Such values may be useful in identifying corrosion or analyzing the extent of corrosion to the set cement. For example, $CO_2$ corrosion proceeds by forming carbonic acid that reacts with analytes in the set cement (e.g., calcium oxide) to form carbonates and bicarbonates, which may increase the porosity of the set cement. Therefore, the concentration of calcium oxide, carbonates, bicarbonates, and the like associated with $CO_2$ corrosion may be useful in monitoring and/or determining the extent of corrosion. Understanding the level of corrosion may allow for taking remedial actions (e.g., performing a remedial cementing operation) before the set cement fails.

Example Embodiments

Example embodiments include the following:

A method comprises optically interacting a set cement with a chemical filter and a detector that together are configured to detect a characteristic of the set cement. Optically interacting the set cement with the chemical filter comprises absorbing, by the chemical filter, at least a portion of an electromagnetic radiation having optically interacted with the set cement. An output signal corresponding to the characteristic of the set cement detected by the chemical filter and the detector is generated. The output signal is received and processed with a signal processor to yield a value for the characteristic of the set cement. A presence or an extent of corrosion to the set cement is determined based on the value of the characteristic of the set cement.

The method further comprises optically interacting an electromagnetic radiation with the set cement to produce an optically interacted electromagnetic radiation that optically interacts with the chemical filter and a detector and modulating the electromagnetic radiation according to a thermal thickness of a sensing layer in the chemical filter. The presence of extent of corrosion is correlated with a location of the set cement. The characteristic of the set cement is a concentration of an analyte. The analyte is selected from the group consisting of calcium oxide, carbonate, and bicarbonate. A remedial operation is performed on the set cement based on the presence or extent of the corrosion. The chemical filter comprises a sensing layer comprising one or more films. The set cement is in an annulus defined by a wellbore and a casing. The output signal is a reflected electromagnetic radiation, a transmitted electromagnetic radiation, or a dispersed electromagnetic radiation.

An apparatus comprises an optical analysis device comprising at least one chemical filter and at least one detector, a signal processor, a processor, and a computer-readable medium having instructions stored thereon that are executable by the processor. The instructions cause the apparatus to optically interact a set cement with the optical analysis device to detect a characteristic of the set cement. Optically interacting the set cement with the optical analysis device comprises absorbing, by the at least one chemical filter, at least a portion of an electromagnetic radiation having optically interacted with the set cement. An output signal corresponding to the characteristic of the set cement detected by the at least one chemical filter and the at least one detector is generated. The output signal is received and processed with the signal processor to yield a value for the characteristic of the set cement. A presence or an extent of corrosion to the set cement is determined based on the value of the characteristic of the set cement.

The instructions further cause the apparatus to optically interact an electromagnetic radiation with the set cement to produce an optically interacted electromagnetic radiation that optically interacts with the at least one chemical filter and the at least one detector and modulate the electromagnetic radiation according to a thermal thickness of a sensing layer in the at least one chemical filter. The presence of the extent of corrosion is correlated with a location of the set cement. An electromagnetic radiation source is arranged to optically interact light with the set cement, the at least one chemical filter, and the at least one detector. The characteristic of the set cement is a concentration of an analyte. The analyte is selected from the group consisting of calcium oxide, carbonate, and bicarbonate. The instructions further cause the apparatus to perform a remedial operation on the set cement based on the presence or the extent of corrosion. At least one chemical filter comprises a sensing layer comprising one or more films. The output signal is a reflected electromagnetic radiation, a transmitted electromagnetic radiation, or a dispersed electromagnetic radiation.

A non-transitory, computer-readable medium has instructions stored thereon that are executable by a computing device to perform operations comprising optically interacting a set cement with a chemical filter and a detector that together are configured to detect a characteristic of the set cement. Optically interacting the set cement with the chemical filter comprises absorbing, by the chemical filter, at least a portion of an electromagnetic radiation having optically interacted with the set cement. An output signal corresponding to the characteristic of the set cement detected by the chemical filter and the detector is generated. The output signal is received and processed with a signal processor to yield a value for the characteristic of the set cement. A presence or an extent of corrosion on the set cement is determined based on the value of the characteristic of the set cement.

The instructions further comprise instructions to optically interact an electromagnetic radiation with the set cement to produce an optically interacted electromagnetic radiation that optically interacts with the chemical filter and a detector and modulate the electromagnetic radiation according to a thermal thickness of a sensing layer in the chemical filter. The presence or the extent of corrosion is correlated with a location of the set cement. A remedial operation is performed on the set cement based on the presence or the extent of corrosion.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The invention claimed is:

1. A method comprising:
   optically interacting an electromagnetic radiation with a set cement to produce an optically interacted electromagnetic radiation that optically interacts with a chemical filter and a detector;
   modulating the electromagnetic radiation according to a thermal thickness of a sensing layer in the chemical filter;
   optically interacting the set cement with the chemical filter and the detector that together are configured to detect a characteristic of the set cement, wherein optically interacting the set cement with the chemical filter comprises absorbing, by the chemical filter, at least a portion of the electromagnetic radiation having optically interacted with the set cement;
   generating an output signal corresponding to the characteristic of the set cement detected by the chemical filter and the detector;
   receiving and processing the output signal with a signal processor to yield a value for the characteristic of the set cement; and
   determining a presence or an extent of corrosion to the set cement based on the value of the characteristic of the set cement.

2. The method of claim 1, further comprising correlating the presence or the extent of corrosion with a location of the set cement.

3. The method of claim 1, wherein the characteristic of the set cement is a concentration of an analyte, the analyte being selected from the group consisting of calcium oxide, carbonate, and bicarbonate.

4. The method of claim 1, further comprising performing a remedial operation on the set cement based on the presence or the extent of corrosion.

5. The method of claim 1, wherein the chemical filter comprises a sensing layer comprising one or more films.

6. The method of claim 1, wherein the set cement is in an annulus defined by a wellbore and a casing.

7. The method of claim 1, wherein the output signal is a reflected electromagnetic radiation, a transmitted electromagnetic radiation, or a dispersed electromagnetic radiation.

8. An apparatus comprising:
   an optical analysis device comprising at least one chemical filter and at least one detector;
   a signal processor;
   a processor; and
   a computer-readable medium having instructions stored thereon that are executable by the processor to cause the apparatus to,
      optically interact an electromagnetic radiation with a set cement to produce an optically interacted electromagnetic radiation that optically interacts with the at least one chemical filter and the at least one detector,
      modulate the electromagnetic radiation according to a thermal thickness of a sensing layer in the at least one chemical filter,
      optically interact the set cement with the optical analysis device to detect a characteristic of the set cement, wherein the instructions comprise instructions to cause absorption, by the at least one chemical filter, of at least a portion of the electromagnetic radiation having optically interacted with the set cement,
      generate an output signal corresponding to the characteristic of the set cement detected by the at least one chemical filter and the at least one detector,
      process the output signal with the signal processor to yield a value for the characteristic of the set cement, and
      determine a presence or an extent of corrosion to the set cement based on the value of the characteristic of the set cement.

9. The apparatus of claim 8, wherein the computer-readable medium further comprises instructions executable by the processor to cause the apparatus to correlate the presence or the extent of corrosion with a location of the set cement.

10. The apparatus of claim 8, further comprising an electromagnetic radiation source arranged to optically interact light with the set cement, the at least one chemical filter, and the at least one detector.

11. The apparatus of claim 8, wherein the characteristic of the set cement is a concentration of an analyte, the analyte being selected from the group consisting of calcium oxide, carbonate, and bicarbonate.

12. The apparatus of claim 8, wherein the computer-readable medium further comprises instructions executable by the processor to cause the apparatus to perform a remedial operation on the set cement based on the presence or the extent of corrosion.

13. The apparatus of claim 8, wherein the at least one chemical filter comprises a sensing layer comprising one or more films.

14. The apparatus of claim 8, wherein the output signal is a reflected electromagnetic radiation, a transmitted electromagnetic radiation, or a dispersed electromagnetic radiation.

15. A non-transitory, computer-readable medium having instructions stored thereon that are executable by a computing device to perform operations comprising:
   optically interacting an electromagnetic radiation with a set cement to produce an optically interacted electromagnetic radiation that optically interacts with a chemical filter and a detector;

modulating the electromagnetic radiation according to a thermal thickness of a sensing layer in the chemical filter;

optically interacting the set cement with an optical analysis device, wherein the optical analysis device comprises the chemical filter and the detector that together are configured to detect a characteristic of the set cement, wherein the instructions to cause the computing device to optically interact the set cement with the optical analysis device comprise instructions to cause absorption, by the chemical filter, of at least a portion of the electromagnetic radiation having optically interacted with the set cement;

generating an output signal corresponding to the characteristic of the set cement detected by the chemical filter and the detector;

processing the output signal with a signal processor to yield a value for the characteristic of the set cement; and determining a presence or an extent of corrosion to the set cement based on the value of the characteristic of the set cement.

16. The non-transitory, computer-readable medium of claim 15, further comprising instructions executable by the computing device to perform operations comprising correlating the presence or the extent of corrosion with a location of the set cement.

17. The non-transitory, computer-readable medium of claim 15, further comprising instructions executable by the computing device to perform operations comprising performing a remedial operation to the set cement based on the presence or the extent of corrosion.

* * * * *